United States Patent
Chou et al.

(10) Patent No.: US 10,823,644 B2
(45) Date of Patent: Nov. 3, 2020

(54) REAL-TIME ON-SITE GAS ANALYSIS NETWORK FOR AMBIENT AIR MONITORING AND ACTIVE CONTROL AND RESPONSE

(71) Applicant: TricornTech Taiwan, Taipei (TW)

(72) Inventors: Tsung-Kuan A. Chou, San Jose, CA (US); Chien-Lin Huang, Sinjhuang (TW); Li-Peng Wang, Taipei (TW)

(73) Assignee: TRICORNTECH TAIWAN, Taipei (TW)

( * ) Notice: Subject to any disclaimer, the term of this patent is extended or adjusted under 35 U.S.C. 154(b) by 0 days.

(21) Appl. No.: 15/248,973

(22) Filed: Aug. 26, 2016

(65) Prior Publication Data
US 2016/0363516 A1 Dec. 15, 2016

Related U.S. Application Data

(62) Division of application No. 14/190,816, filed on Feb. 26, 2014.
(Continued)

(51) Int. Cl.
*G01N 30/86* (2006.01)
*G01N 1/26* (2006.01)
(Continued)

(52) U.S. Cl.
CPC .............. *G01N 1/26* (2013.01); *G01N 30/88* (2013.01); *G01N 33/0031* (2013.01);
(Continued)

(58) Field of Classification Search
CPC ...... G01N 1/26; G01N 30/88; G01N 33/0031; G01N 33/0075; G01N 2030/8881; G01N 2001/021
(Continued)

(56) References Cited

U.S. PATENT DOCUMENTS

| 4,204,121 A | 5/1980 | Milly |
| 4,499,377 A | 2/1985 | Presser |

(Continued)

FOREIGN PATENT DOCUMENTS

| CN | 1566944 | 1/2005 |
| CN | 201256559 Y | 6/2009 |

(Continued)

OTHER PUBLICATIONS

PCT/US2014/019571; PCT International Preliminary Report on Patentability, dated Sep. 11, 2015, 9 pages.
(Continued)

*Primary Examiner* — Daniel S Larkin
(74) *Attorney, Agent, or Firm* — Womble Bond Dickinson (US) LLP

(57) ABSTRACT

Embodiments of an apparatus comprising a plurality of multiple-gas analysis devices positioned within a relevant area, each multiple-gas analysis device capable of detecting the presence, concentration, or both, of one or more gases. A data and control center is communicatively coupled to each of the plurality of multiple-gas analysis device, the data and control system including logic that, when executed, allows the data and control center to monitor readings from the plurality of multiple-gas analysis devices and if any readings indicate the presence of one or more contaminants, identifying the source of the contaminants based on the readings from the plurality of multiple-gas analysis devices.

15 Claims, 10 Drawing Sheets

Related U.S. Application Data

(60) Provisional application No. 61/770,978, filed on Feb. 28, 2013.

(51) Int. Cl.
  *G01N 30/88* (2006.01)
  *G01N 33/00* (2006.01)
  *G01N 1/02* (2006.01)
  *G01N 30/02* (2006.01)

(52) U.S. Cl.
  CPC ... *G01N 33/0075* (2013.01); *G01N 2001/021* (2013.01); *G01N 2030/025* (2013.01); *G01N 2030/8881* (2013.01)

(58) Field of Classification Search
  USPC .............. 73/31.01, 31.02, 31.03, 31.05, 40
  See application file for complete search history.

(56) References Cited

U.S. PATENT DOCUMENTS

| | | | |
|---|---|---|---|
| 6,053,058 A | | 4/2000 | Hayashi |
| 6,125,710 A | * | 10/2000 | Sharp ..................... G01N 1/26 73/863.01 |
| 6,670,887 B2 | | 12/2003 | Dungan |
| 6,794,991 B2 | | 9/2004 | Dungan |
| 7,147,695 B2 | | 12/2006 | Mitra |
| 2001/0040509 A1 | | 11/2001 | Dungan |
| 2002/0070869 A1 | * | 6/2002 | Dungan ............. G01N 33/0073 340/632 |
| 2004/0194628 A1 | | 10/2004 | Mitra |
| 2006/0234621 A1 | | 10/2006 | Desrochers et al. |
| 2009/0308136 A1 | | 12/2009 | Wang et al. |
| 2010/0042333 A1 | | 2/2010 | Scheffler et al. |
| 2010/0079764 A1 | | 4/2010 | Spartz et al. |
| 2010/0219960 A1 | | 9/2010 | Moe et al. |
| 2011/0005300 A1 | | 1/2011 | Wang et al. |
| 2011/0009986 A1 | | 1/2011 | Page |
| 2011/0023581 A1 | | 2/2011 | Chou et al. |
| 2011/0259081 A1 | | 10/2011 | Chou et al. |
| 2012/0090378 A1 | | 4/2012 | Wang et al. |
| 2013/0036811 A1 | | 2/2013 | Boult |
| 2013/0046485 A1 | | 2/2013 | Norman et al. |
| 2013/0304385 A1 | | 11/2013 | Gilette |

FOREIGN PATENT DOCUMENTS

| | | |
|---|---|---|
| CN | 102207512 A | 10/2011 |
| CN | 202204805 U | 4/2012 |
| EP | 2199790 A1 | 3/2010 |
| JP | 06317508 | 11/1994 |
| JP | 2003106395 A | 4/2003 |
| WO | 0013010 | 3/2000 |
| WO | 0114873 | 3/2001 |
| WO | 2009155125 | 12/2009 |

OTHER PUBLICATIONS

PCT/US2014/019571, PCT International Search Report and Written Opinion, dated Jun. 23, 2014.
CN 201480023613.5—First Office Action with Translation, dated May 5, 2016, 29 pages.
U.S. Appl. No. 14/190,816—Non-Final Office Action, dated May 9, 2016, 7 pages.
U.S. Appl. No. 14/190,816—Non-Final Office Action, dated Oct. 4, 2016, 18 pages.
CN 201480023613.5—Second Office Action with Translation, dated Mar. 7, 2017, 35 pages.
Korean Office Action for Application No. 10-2015-7026704 dated Jun. 26, 2020, 11 pages.
Indian Office Action for Application No. 5151/CHENP/2015 dated May 28, 2020, 6 pages.
European Patent Office Search Report for Application No. 14190816 dated Aug. 14, 2020, 5 pages.

* cited by examiner

REAL-TIME ON-SITE GAS ANALYSIS NETWORK FOR AMBIENT AIR MONITORING AND ACTIVE CONTROL AND RESPONSE

CROSS-REFERENCE TO RELATED APPLICATIONS

This application is a divisional of U.S. application Ser. No. 14/190,816, filed 26 Feb. 2014, which in turn claims priority under 35 U.S.C. § 119(e) to U.S. Provisional Application No. 61/770,978, filed 28 Feb. 2013. The content of both priority applications is hereby incorporated by reference in its entirety.

TECHNICAL FIELD

The present invention relates generally to a gas analysis network and in particular, but not exclusively, to a real-time on-site gas analysis network for ambient air monitoring and active control and response.

BACKGROUND

FIGS. 1A-1B illustrate embodiments of an apparatus and method for real-time gas analysis. FIG. 1A shows a method using multiple gas-chromatography/mass-spectrometer (GC/MS) systems. Conventional GC/MS systems cannot be installed on-site for direct gas analysis, meaning that special gas sampling pipes are used to provide air inlets at regions of interest, such as regions 1-4. Each gas sampling pipe carries gas sampled from its respective region to a corresponding GC/MS system that remains in a central lab. Although GC/MS systems can provide excellent detection sensitivity and specificity on multiple gases analysis, such a setup can be quite expensive to maintain.

FIG. 1B illustrates an alternative method that can be used to reduce cost. Simple portable single-gas detectors are used at specific regions, such as regions 1-4, for direct gas detection. The detected gas concentrations are then collected and stored at a data center. In some embodiments the single-gas detectors are incapable of detecting multiple gases separately, and might also constantly suffer from cross-interference of other gases in the field. These and other characteristic make the illustrated arrangement unsuitable for obtaining reliable gas concentration information for active ambient air monitoring and control.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION OF ILLUSTRATED EMBODIMENTS

Embodiments are described of an apparatus, system and method for a real-time on-site gas analysis network for ambient air monitoring and active control and response. Specific details are described to provide a thorough understanding of the embodiments, but one skilled in the relevant art will recognize that the invention can be practiced without one or more of the described details, or with other methods, components, materials, etc. In some instances, well-known structures, materials, or operations are not shown or described in detail but are nonetheless encompassed within the scope of the invention.

Reference throughout this specification to "one embodiment" or "an embodiment" means that a described feature, structure, or characteristic can be included in at least one described embodiment, so that appearances of "in one embodiment" or "in an embodiment" do not necessarily all refer to the same embodiment. Furthermore, the particular features, structures, or characteristics may be combined in any suitable manner in one or more embodiments.

Embodiments are disclosed below of real-time monitoring and control of ambient air quality by using a network of on-site multiple-gas analysis devices in combination with optional anemometers. The embodiments can be applied to various indoor or outdoor environmental setups. In a semiconductor facility, for instance, the embodiments can be used to ensure the cleanroom air is free of airborne molecular contamination (AMC), which becomes critical as semiconductor processing technology goes below 40 nm nodes because AMC affects device yield. In a steel manufacturing facility, the embodiments can be used to monitor coke oven gas by-product leakage and process optimization. In a petrochemical facility, the embodiments can be used to identify leaking gases and locate the source of leakage, which can provide immediate warning and emergency response actions.

Figure 1A:
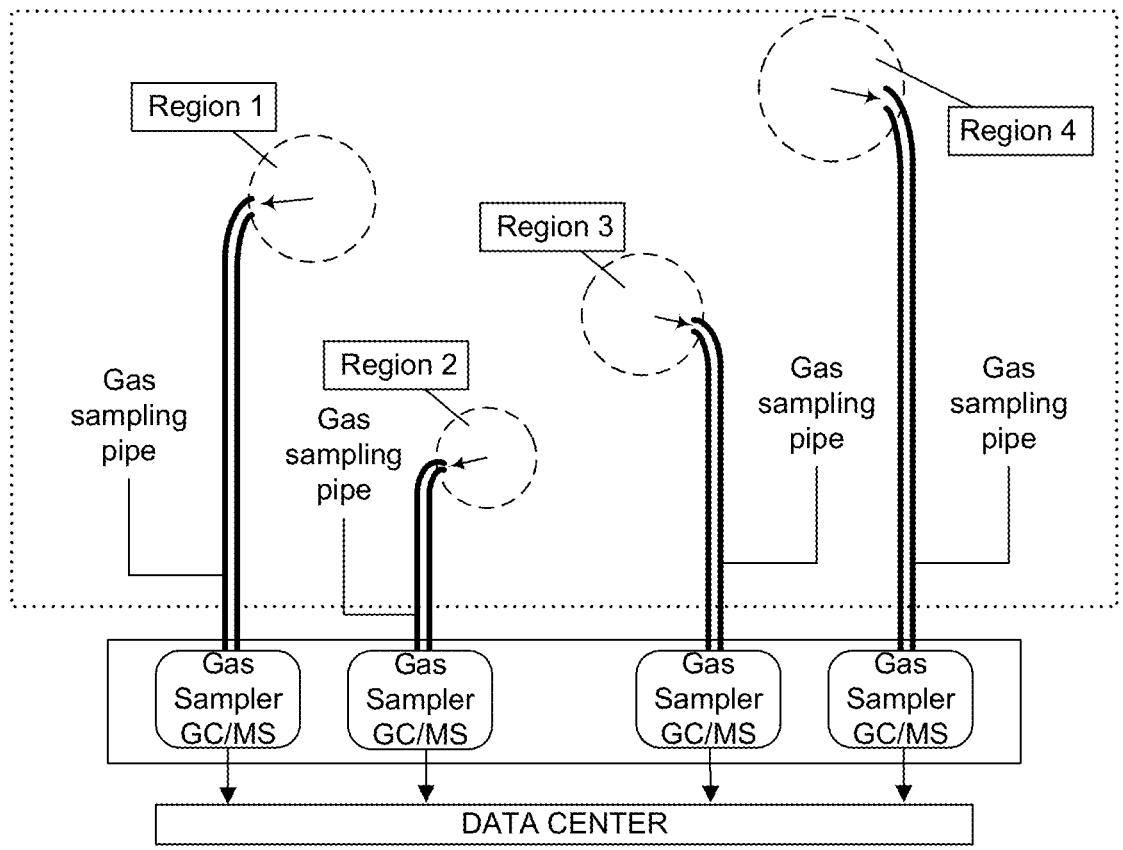
FIGS. 1A-1B are schematics of embodiments of gas monitoring systems.
Figure 1B:
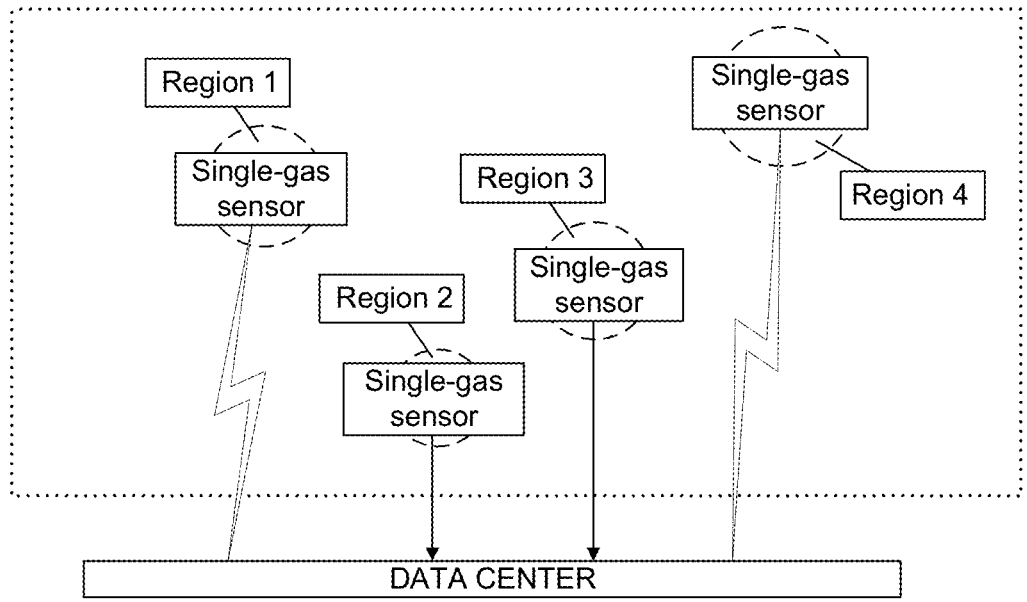
Figure 2A:
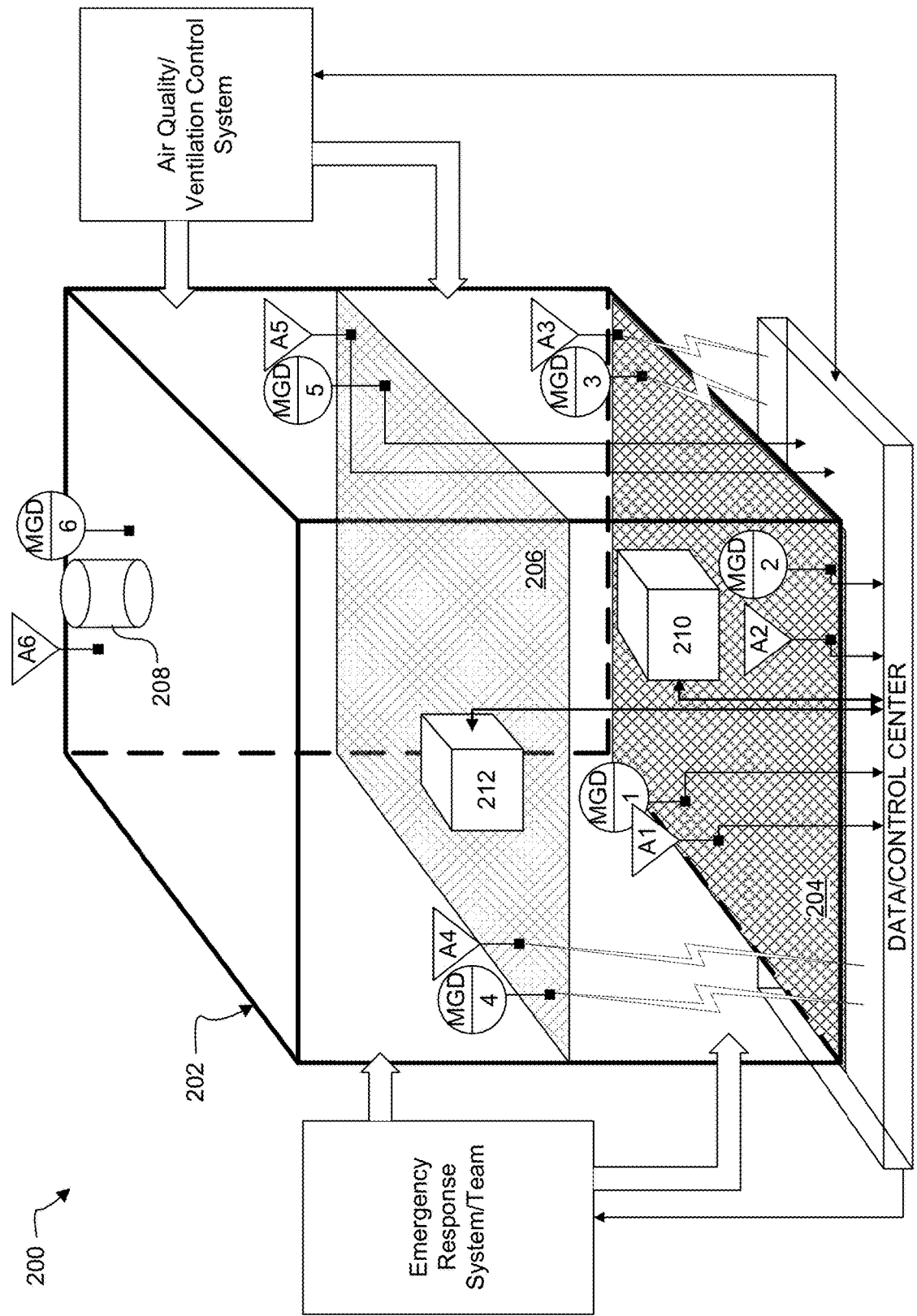
FIG. 2A-2C are schematic drawings of embodiments of an indoor gas monitoring and control system.

FIG. 2A illustrates an embodiment of an environmental monitoring and control system 200 for indoor applications such as semiconductor fabrication facilities, public buildings, etc. A system of multiple gas analysis devices and anemometers are positioned at various indoor locations to form a real-time gas analysis network to monitor the gas concentration and air flow or wind speed and its direction. The gas analysis devices, and anemometers if present, are linked to control/sever/information center for real-time data communication and control.

In system 200, one or more multiple-gas analysis devices (also called multiple-gas detectors, or MGDs) are installed at locations within an enclosed facility 202, such as a building, to detect gases of interest for the specific application of the building. Although described herein as a building, in other embodiments facility 202 can be a subset of a building, for example a room or enclosed space within a building, and in still other embodiments can include multiple buildings. Building 202 can have multiple floors, such as a first floor 204 and a second floor 206, and each floor can have some kind of process equipment or process facility: in the illustrated embodiment, first floor 204 has a process facility 210 and second floor 206 has a process facility 212. In other embodiments, of course, there can be more or less floors than shown, every floor need not include a process facility, each floor can have more or less process facilities than shown, and the process facilities can be positioned differently than shown.

In the illustrated embodiment, MGDs are positioned on different floors of the building, with MGDs 1-3 on first floor 204 and MGDs 4-5 on second floor 206. On each floor where they are located, the MGDs can be vertically positioned anywhere from floor to ceiling, and all MGDs on a given floor can have, but need not have, the same vertical positioning. An MGD such as MGD6 can be positioned on the exterior of building 202, for example near a vent 208. If MGDs in the interior (MGD1-MGD5) detect contamination inside the facility, exterior MGD6 can help assess whether any contaminants are escaping or entering the facility.

Multiple-gas detectors MGD1-MGD6 are capable of detecting organic or non-organic gas compounds, as well as combination of gases of interest for on-site monitoring (organic or non-organic gas compounds). In one embodiment, one or more of the MGDs can be a miniaturized gas analysis system utilizing a combination of micro-pre-concentrator (micro-PC), micro-gas-chromatography (micro-GC), and a detector array for multiple-gas detection, as described below in connection with FIGS. 5A-8.

One or more anemometers can optionally be installed in building 202 to obtain information about the air flow rate, speed, and direction within the building, as well as other characteristics of the air such as temperature, humidity, and pressure. In the illustrated embodiment each MGD is paired with an anemometer and there is a one-to-one correspondence between MGDs and anemometers (i.e., each MGD has a corresponding anemometer). For example MGD1 is paired with anemometer A1, MGD2 is paired with anemometer A2, and so on. But in other embodiments of system 200 the correspondence between multiple-gas detectors and anemometers can be many-to-one instead of one-to-one. The many-to-one correspondence can go both ways: in some embodiments each multiple-gas detector can be paired with a plurality of anemometers, but in other embodiments each anemometer can be paired with a plurality of multiple-gas detectors.

In the illustrated embodiment every MGD has a nearby anemometer, such that each anemometer measures air speed, direction, etc., in the immediate vicinity of its corresponding MGD. But in other embodiments this need not be the case: the anemometers, if present, can be positioned apart from MGD's so that they measure speed, direction, etc., at places in the building other than in the immediate vicinity of an MGD.

Multiple-gas detectors MGD1-MGD6, and anemometers A1-A6 if present, are communicatively coupled to a data/control center via wired or wireless communication. All the MGDs, and anemometers if present, need not be communicatively coupled to the data/control center the same way; some can be communicatively coupled by wire, others wirelessly. By communicatively coupling the MGDs and anemometers to the data center, the instruments can provide the data and control center with the real-time data and updates.

One or more servers in the data and control center collect and analyze readings from the MGDs and anemometers to determine real-time on-site gas concentration at different locations within the facility. The data and control center can provide information analysis, data storage, and corresponding terminal systems feedback and control. The control center analyzes the gas concentration data from MGDs together with the air flow, wind speed, etc., and surrounding obstacles (or topography) and derives a real-time gas concentration distribution map of the whole area of interest. The data center can determine whether there is an abnormal increase of contaminants or gas leakage and can trigger immediate warnings and further identify the location of a specific machine or pipe, for example, that might be causing the change of air quality.

In addition to being communicatively coupled to the MGD's and anemometers if present, the data and control center can be communicatively coupled, by wire or wireless link, to process facilities 210 and 212 within building 202, or to specific components within a process facility. The data and control center can additionally be communicatively coupled to the building's ventilation system, and to an emergency response team.

If communicatively coupled to process facilities 210 and 212 within building 202, or to elements within the process facilities, the data and control system can determine the process facility or machine from which gas leakage is occurring and turn off the system to reduce or cease leakage. For example, the control center can be linked and can remotely adjust the facility or system that is determined to be out of spec back to its optimum condition to produce best process yield. If linked to a ventilation system, the data and control center can control the ventilation system or specific elements within a ventilation system such as pumps, fans, individual vents, duct closures, etc., to immediately reduce the contaminant concentration and prevent any catastrophic events or consequences that could occur due the increase of contaminant gases.

If linked to an emergency response system, the data and control center can provide immediate warning and corresponding action upon detecting contaminants. The data and control center can then notify a response team and direct it to the site of contamination source. The response team can send personnel to the site of abnormal gas outbreak for further test and confirmation, which can then be fed back to control center for close-loop data analysis validation and improvement.

Figure 2B:
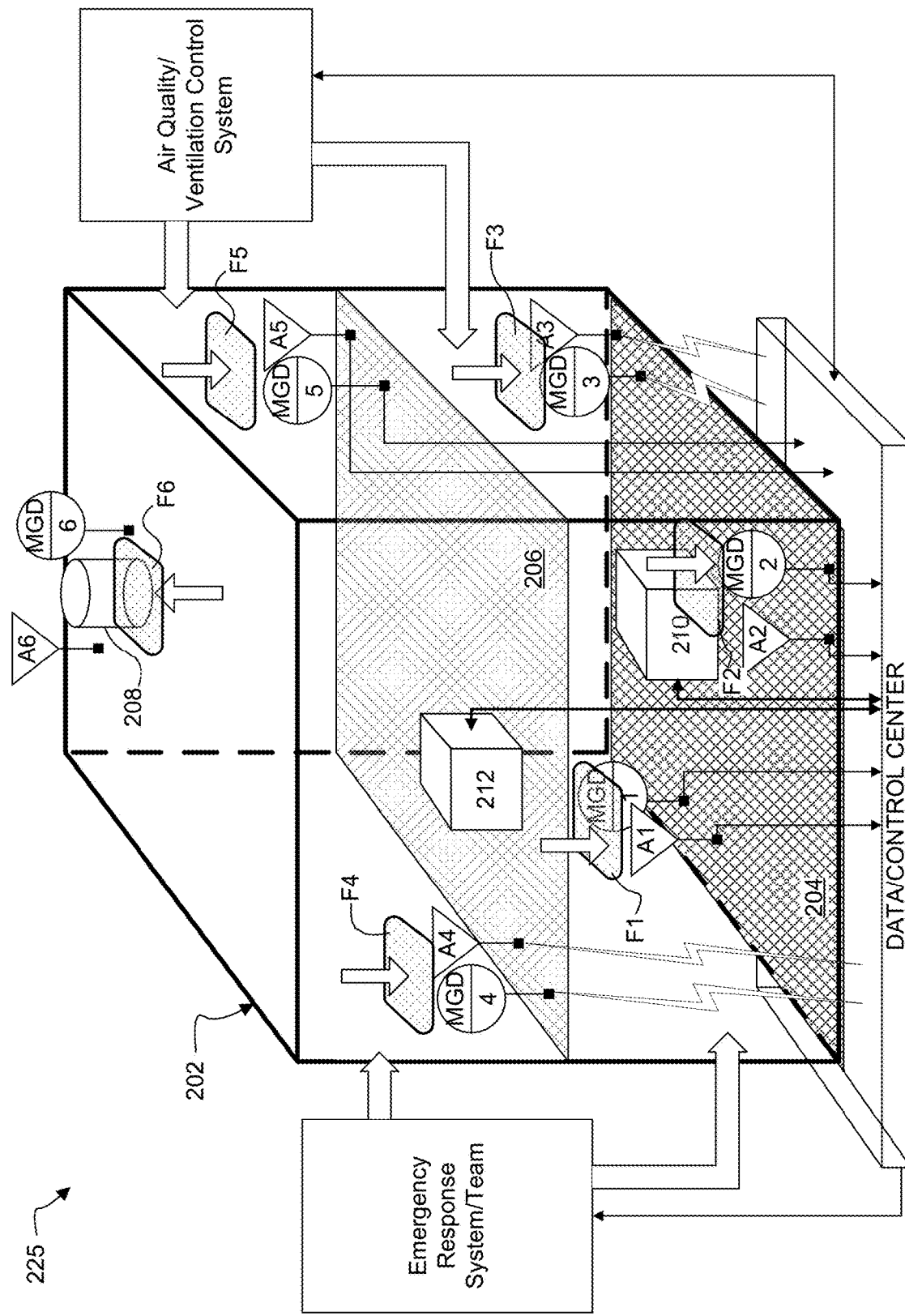

FIG. 2B illustrates another embodiment of an environmental monitoring and control system 225 for indoor applications. System 225 is in most respects similar in features and function to system 200. The primary difference between systems 225 and 200 is that in system 225 each MGD is located at or near the output of different air filters F1-F6, which can be used to filter incoming air from outside the building or outgoing air that exits the building. In one embodiment the filters are part of the air quality/ventilation system of building 202, but in other embodiments the filters can be part of another system, whether related to the building or not. In system 225 each filter is positioned above an MGD, but in other embodiments the filters need not be positioned above, but can instead be positioned below or to the side of the MGD. An MGD such as MGD6 can be positioned on the exterior of building 202, for example near exiting building through vent 208. A filter F6 can be positioned over vent 208 to filter air exiting building 202, and MGD6 can help assess whether any contaminants are escaping the facility and, as a result, whether filter F6 needs re-placement. An MGD such as MGD5 can be positioned at the interior of building 202, for example at or near a location where air enters building 202 through an air inlet from the ventilation control system. Filter F5 can be positioned to filter contaminants from outside air entering building 202, and MGDS can help assess whether any contaminants are entering the facility and, as a result, whether filter F5 needs re-placement.

In the illustrated embodiment every MGD is coupled to a corresponding air filter, meaning that there is a one-to-one correspondence between MGDs and filters: MGD1 is coupled to filter F1, MGD2 is coupled to filter F2, and so on. But in other embodiments the correspondence can be many-to-one instead of one-to-one: there can be more than one MGD per filter, or more than one filter per MGD. As in system 200, in system 225 the MGDs can optionally be paired with anemometers, with a one-to-one correspondence as shown or with a many-to-one correspondence of MGDs to anemometers or anemometers to MGDs.

In system 225, each MGD can monitor the output quality of air passing through the corresponding filter. When the concentration of contaminants (e.g., volatile organic compounds, or VOCs) is beyond the threshold on any MGD, at least one will be able to determine the specific filter that is no longer filtering satisfactorily and needs to be replaced. This approach will greatly reduce unneeded filter replacement and thus minimize the cost of replacement.

Figure 2C:
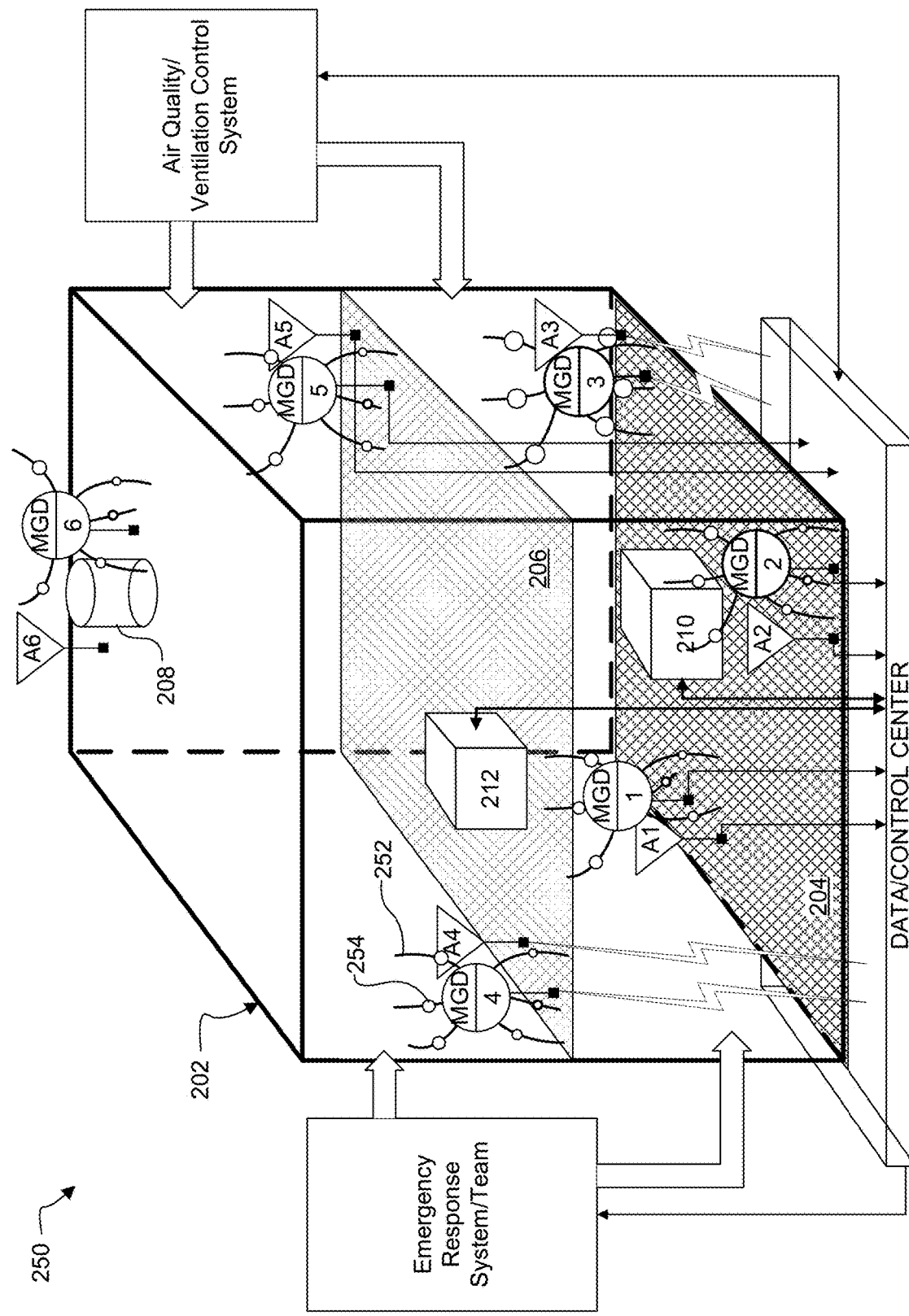

FIG. 2C illustrates another embodiment of an environmental monitoring and control system 250 for indoor applications. System 250 is in most respects similar in features and function to system 200. The primary difference between systems 250 and 200 is that in system 250 each MGD includes multiple sampling tubes that extended to different locations of the MGD's individual region. For instance, MGD 4 includes a plurality of sampling tubes 252 having one end coupled to MGD4 and its other end, the sampling end through which air is drawn, extending away from MGD4. In the illustrated embodiment of system 250 each MGD is coupled to six sampling tubes, but in other embodiments each MGD can be coupled to more or less sampling tubes, and every MGD need not have the same number of sampling tubes.

Each sampling tube 252 can also include a VOC or gas sampler, such as sorbent trap 254, through which air collected by the sampling tube can flow. This approach allows one to sample the air at more specific locations with higher spatial coverage density. The sample collection and analysis can be multiple modes. In MGD4, every sampling tube 252 includes a sorbent trap, but in other embodiments less than all tubes can include sorbent traps, or no tubes at all can include sorbent traps. Moreover, every MGD need not include sorbent traps and, if an MGD does include them, need not include the same number of sorbent traps as other MGDs.

For embodiments without sorbent traps 254, the air sampling can be done by collecting air from all tubes simultaneously and analyzed by the MGD, which will provide the overall contaminant concentration of the area covered by one MGD. In another mode, the air sampling and analysis can be done in series for each sampling tube (e.g., sample tube #1 and analyze to determine contaminant concentration at sampling tube #1's location, and repeat for other sampling tubes), which will provide the more detail contaminant concentration at each specific location. For embodiments with sorbent traps 254, the air sampling can be done simultaneously with the contaminants are separately collected by each sorbent trap. The contaminants in each sorbent trap can then be desorbed to the MGD for analysis in sequence for separate analysis.

Figure 3A:
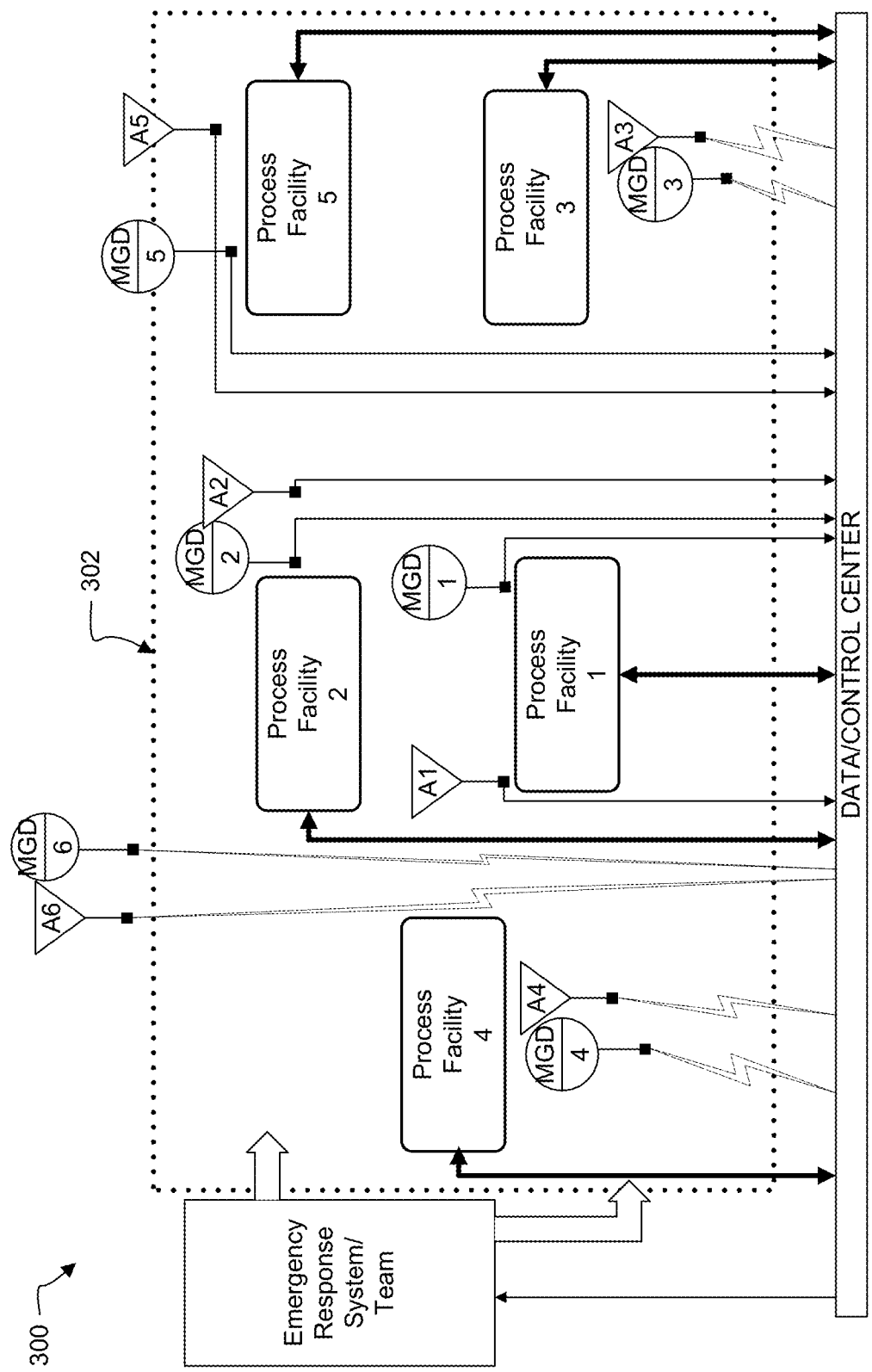
FIGS. 3A-3B are schematic drawings of embodiments of an outdoor gas monitoring and control system.

FIG. 3A illustrates an embodiment of an outdoor monitoring and control system 300 that can be useful for applications such as petrochemical plants and steel coke ovens. System 300 is in most respects similar to system 200: multiple gas analysis devices and anemometers are positioned at various locations to form a real-time gas analysis network to monitor the gas concentration and air flow or wind speed and its direction. The gas analysis devices and/or anemometers are linked to control/sever/information center for real-time data communication and control.

In system 300, one or more multiple-gas analysis devices (also called multiple-gas detectors, or MGDs) are installed at locations within a region of interest 302 surrounding an outdoor facility such as a petrochemical plant. Process facilities 1-5 are positioned within region of interest 302. In other embodiments, of course, there can be more or less process facilities than shown, and the process facilities can be positioned differently than shown.

In the illustrated embodiment, MGDs are positioned near process facilities within a relevant area or region of interest 302, with MGDs 1-5 near process facilities 1-5. Wherever they are located, the MGDs can be vertically positioned anywhere from the floor to some height above the process facility, and all MGDs in a given region 302 can have, but need not have, the same vertical positioning. An MGD such as MGD6 can be positioned outside region of interest 302. If MGDs inside region of interest 302 (MGD1-MGD5) detect contamination inside the region of interest, exterior MGD6 can help assess whether any contaminants are drifting out of the region of interest. The MGDs used in system 300 can have the same characteristics and capabilities as the MGDs used in system 200.

One or more anemometers can optionally be installed in relevant area 302 to obtain information about the air flow rate, speed, and direction within the area, as well as other characteristics of the air such as temperature, humidity, and pressure. In the illustrated embodiment each MGD is paired with an anemometer and there is a one-to-one correspondence between MGDs and anemometers (i.e., each MGD has a corresponding anemometer). For example MGD1 is paired with anemometer A1, MGD2 is paired with anemometer A2, and so on. But in other embodiments of system 200 the correspondence between multiple-gas detectors and anemometers can be many-to-one instead of one-to-one. The many-to-one correspondence can go both ways: in some embodiments each MGD can be paired with a plurality of anemometers, but in other embodiments each anemometer can be paired with a plurality MGDs.

In the illustrated embodiment every MGD has a nearby anemometer, such that each anemometer measures air speed, direction, etc., in the immediate vicinity of its corresponding MGD. But in other embodiments this need not be the case: the anemometers, if present, can be positioned apart from MGD's so that they measure speed, direction, etc., at places other than in the immediate vicinity of an MGD.

Multiple-gas detectors MGD1-MGD6, and anemometers A1-A6 if present, are communicatively coupled to a data/control center via wired or wireless communication. All the MGDs, and anemometers if present, need not be communicatively coupled to the data/control center the same way; some can be communicatively coupled by wire, others wirelessly. By communicatively coupling the MGDs and anemometers to the data center, the instruments can provide the data and control center with the real-time data and updates.

As in system 200, one or more servers in the data and control center collect and analyze readings from the MGDs and anemometers to determine real-time on-site gas concentration at different locations within the region of interest and provide information analysis, data storage, and corresponding terminal systems feedback and control. The control center analyzes the gas concentration data from distributed devices in the network together with the air flow or wind speed, and surrounding obstacles (or topography) and derives a real-time gas concentration distribution map of the whole area of interest. The data center can determine whether there is an abnormal increase of contaminants or gas leakage and can trigger immediate warnings and further identify the location of a machine or pipe, for example, that might be causing the change of air quality. The control center can determine the ambient air quality and also identify the location of gas leakage and whether it is within the area of concern, which in turn prevents false alarms.

In addition to being communicatively coupled to the MGD's and anemometers if present, the data and control center can be communicatively coupled, by wire or wireless link, to process facilities 1-5 within area 302, and can additionally be communicatively coupled to an emergency response team. As in system 200, in system 300 the control center can also be communicatively coupled process facilities 210 and 212 within building 202, or to elements within the process facility, from which gas leakage is occurring and turn off the system to reduce or cease leakage. For example, the control center can be linked and can (remotely) adjust the facility or system that is determined out of spec back to its optimum condition to produce best process yield.

The control center can be linked with emergency response system and provide immediate warning and corresponding action. The data and control center can then notify a response team and direct it to the site of contamination source. The corresponding action team can send personnel to the site of abnormal gas outbreak for further test and confirmation, which can then be fed back to control center for close-loop data analysis validation and improvement.

With the real-time on-site gas concentration at different locations of the manufacturing plants or locations of interest, the data center can continuously determine a synchronized gas distribution based on wind information and buildings/obstacles or surrounding topography and determine whether there is any abnormal increase of specific gases or hazardous gas leakage. For an abnormal increase of a specific gas, which may correspond to decrease of production efficiency as identified by data center, the control center can directly control the specific facility operation to ensure the system is back at optimum condition. For an abnormal increase of specific gas, which may correspond to a hazardous gas leakage, the control center can identify the location or source of gas leakage based on the gas concentration distribution data map and then provide necessary warning and direct a response team to the site of problem.

Figure 3B:
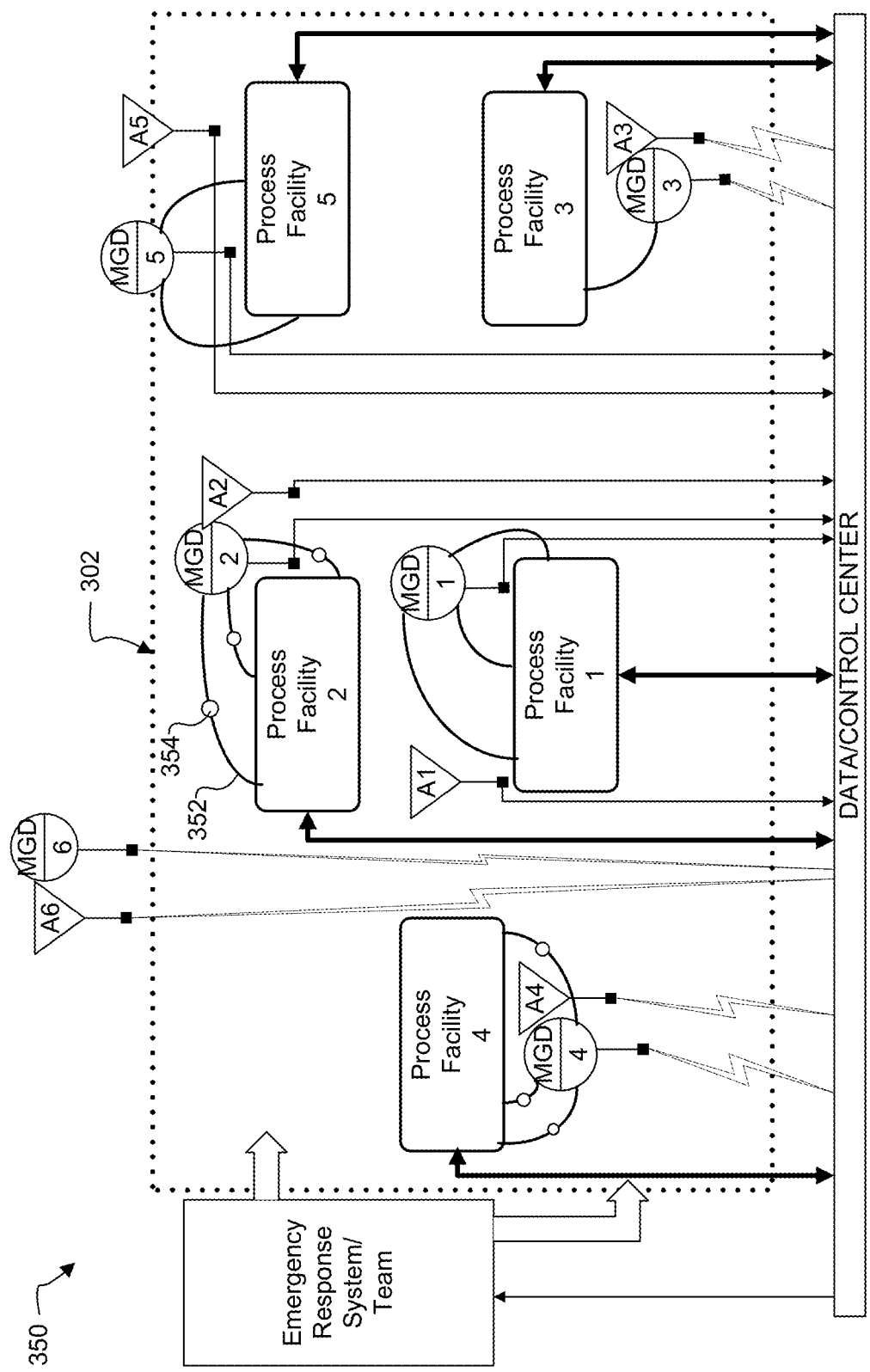

FIG. 3B illustrates another embodiment of an environmental monitoring and control system 350 for outdoor applications. System 350 is in most respects similar in features and function to system 300. The primary difference between systems 350 and 300 is that in system 350 each MGD includes multiple sampling tubes that can extend into or near the process facility with which the MGD is associated. For instance, MGD2 includes a plurality of sampling tubes 352 having one end coupled to MGD2 and its other end, the sampling end through which air is drawn, extending into or near process facility 2. In the illustrated embodiment of system 350, MGD2 is coupled to three sampling tubes, but each MGD can be coupled to more or less sampling tubes, and every MGD in system 350 need not have the same number of sampling tubes.

Each sampling tube 352 can also include a VOC sampler, such as sorbent trap 354, through with air collected by the sampling tube can flow. This approach allows one to sample the air at more specific locations with higher spatial coverage density. The sample collection and analysis can be multiple modes. In MGD4, every sampling tube 352 includes a sorbent trap, but in other embodiments less than all tubes can include sorbent traps, or no tubes at all can include sorbent traps. Moreover, every MGD need not include sorbent traps and, if an MGD does include them, need not include the same number of sorbent traps as other MGDs.

For embodiments without sorbent traps 354, the air sampling can be done by collecting air from all tubes simultaneously and analyzing them with the MGD; this will provide the overall contaminant concentration of the area covered by one MGD. In another mode, the air sampling and analysis can be done in series for each sampling tube (e.g., sample tube #1 and analyze to determine contaminant concentration at sampling tube #1's location, and repeat for other sampling tubes), which will provide the more detail contaminant concentration at each specific location. For embodiments with sorbent traps 354, the air sampling can be done simultaneously with the contaminants are separately collected by each sorbent trap. The contaminants in each sorbent trap can then be desorbed to the MGD for analysis in sequence for separate analysis.

Figure 4:
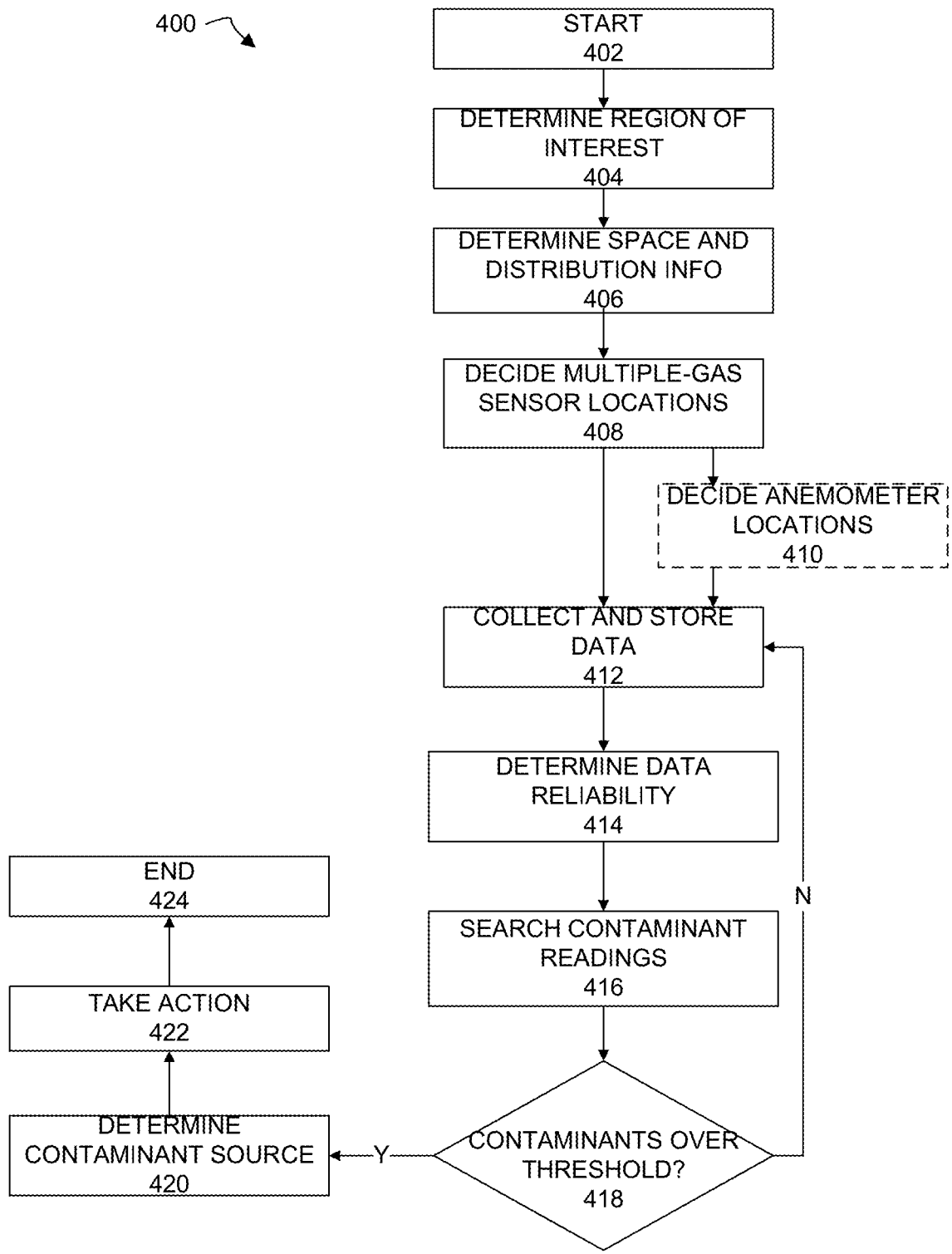
FIG. 4 is a flowchart of an embodiment of a process for setting up and operating an indoor or outdoor gas monitoring and control system.

FIG. 4 illustrates an embodiment of a process 400 for setting up and operating gas analysis systems, such as systems 200 and 300. Such a setup can be applied to the following industries (but not limited by those industries) for targeted ambient air monitoring and control in order to achieve optimum manufacturing efficiency and yield output as well as excess waste by-product exhaust or toxic gas leak warning: semiconductor manufacturing fab, display manufacturing, PCB fab, steel coke oven plants, and petrochemical plants.

The process starts at block 402. At block 404, the region of interest, whether indoor or outdoor, is identified. At block 406, the process conducts analysis on space and geographic distribution info for the area of interest on possible gas contaminants or gases of concern, as well as topographical information on obstructions and other objects within the region of interest.

At block 408, based on the analysis performed at block 406 the process makes a decision on optimum multiple-gas detector detection specification, number of devices, and placement locations and construction of gas sensing network. At block 410, which is optional as indicated by the dashed outline, the process uses the analysis performed at block 406 to decide the number and placement of anemometers within the relevant area.

Operation of the monitoring system begins at block 412, with automatic real-time monitoring data collection and storage at control center. At block 414, automatic data analysis on the reliability of gas monitoring data from each device is performed to ensure no false data due to device or data communication glitches. At block 416, the process searches for source location of abnormal gas concentration level based on analysis of gases data (in combination with air flow, wind speed, direction, etc., and area topography if anemometers are used). At block 418, the process determines whether the source location has gas concentrations over threshold level. If at block 418 the process determines that the gas concentrations do not exceed the threshold, the process returns to block 412, where it continues to collect and store data. But if at block 418 the process determines that the gas concentrations do exceed the threshold, at block 420 the available data from all MGD's, and anemometers if present, is used to identify the contamination source. At block 422, the process takes action such as controlling the ventilation system and/or process facilities for an indoor application, controlling the process facilities for an outdoor application, and provide necessary warning to corresponding party for necessary action in either indoor or outdoor applications. For situation that there are many possible sources of gas leakage systems and same location without an individual gas device to differentiate the gas leakage on-site, personnel may be sent to perform an on-site test on each system with a portable gas detector to confirm the actual problematic system. At block 424, process 400 ends.

Figure 5A:
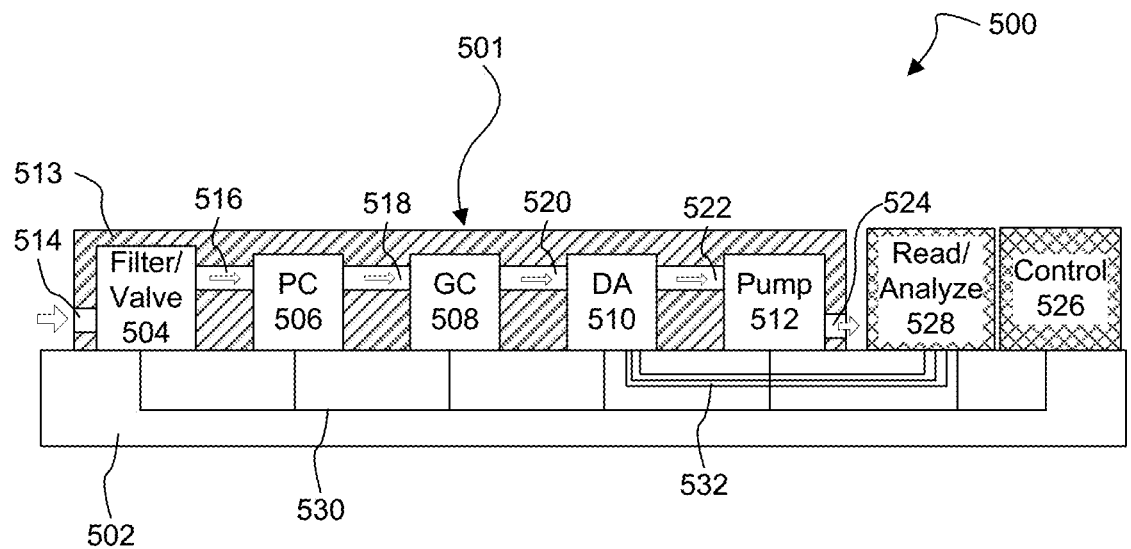
FIGS. 5A-5B are side view and plan view schematics of an embodiment of a multiple-gas analysis system that can be used in the indoor and outdoor gas monitoring and control systems of FIGS. 2-3.
Figure 5B:
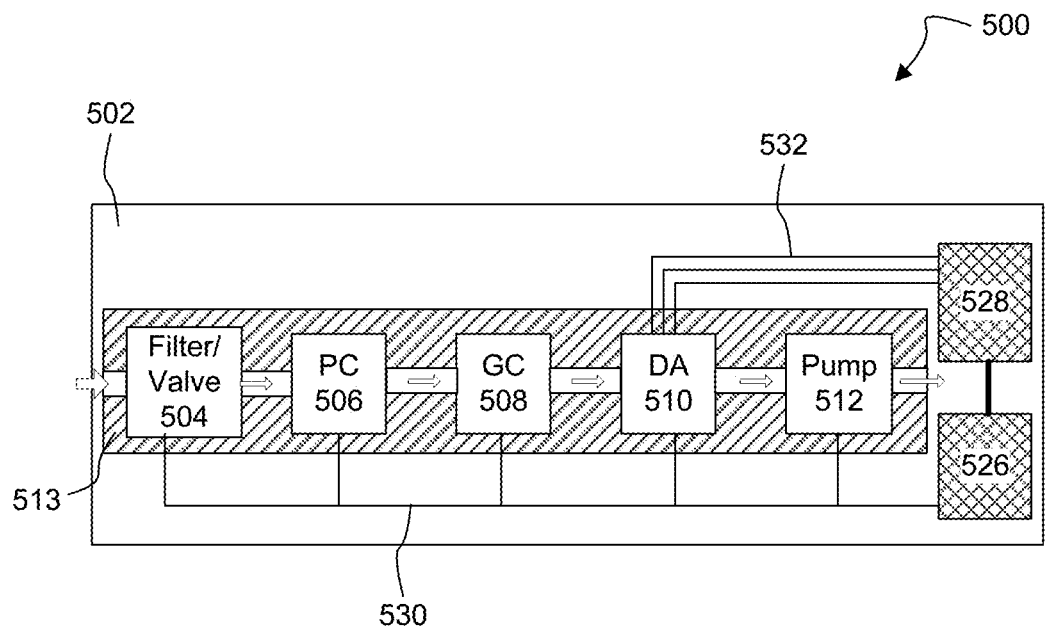

FIGS. 5A-5B schematically illustrate an embodiment of a multiple-gas detection and analysis device that can be implemented in the above-described environmental detection and control systems. A commercial embodiment of the illustrated multiple-gas analysis device, known as MiTAP, is developed by TricornTech Taiwan & TricornTech Corporation of San Jose, Calif. MiTAP can provide more frequent gas concentration distributions for data analysis, which in turn gives the control center much faster update of ambient air condition at corresponding field site. As a result, a more precise active control of air quality can be achieved for consistent robust manufacturing yield, which can be extremely crucial in manufacturing processes such as semiconductor production. Meanwhile, for toxic gas leakage monitoring, MiTAP can provide much faster update/warning on the event of gas leakage, which can be crucial to prevent life-threatening system failures at the manufacturing site.

As further described below, MiTAP utilizes micro-pre-concentration (micro-PC), micro-gas-chromatography (micro-GC), and detector array (DA) technology for direct air sampling and gas analysis as described, for example, in U.S. Patent Publication Nos. 2009/0308136, 2011/0005300, 2011/0023581, 2011/0259081, and 2012/0090378, all of which are hereby incorporated by reference in their entirety). It is a portable and stand-along device that does not require expensive laboratory gas supplies and piping setups, but unlike conventional GC/MS systems, it can be installed on-site and is able to perform direct gas sampling for multiple-gas analysis with performance similar to GC/MS system in the laboratory. The device has capability to separate and detect more than 50 volatile organic compounds (VOCs) in each 15-min test (but not limited to VOCs), which can provide much more real-time data points for faster active control and response compared to conventional GC/MS system method for gas analysis.

FIGS. 5A-5B together illustrate an embodiment of a small-scale multiple-gas analysis device 500. MGD 500 includes a substrate 502 on which are mounted a fluid handling assembly 501, a controller 526 coupled to the individual elements within fluid handling assembly 501, and a reading and analysis circuit 528 coupled to detector array 510 and to controller 526. The embodiment shown in the figures illustrates one possible arrangement of the elements on substrate 502, but in other embodiments the elements can, of course, be arranged on the substrate differently.

Substrate 502 can be any kind of substrate that provides the required physical support and communication connections for the elements of device 500, such as a single-layer or multi-layer printed circuit board (PCB) with conductive traces or a chip or wafer made of silicon or some other semiconductor. In still other embodiments, substrate 502 can also be a chip or wafer in which optical waveguides can be formed to support optical communication between the components of device 500.

Fluid handling assembly 501 includes a filter and valve assembly 504, a pre-concentrator 506, a gas chromatograph 508, a detector array 510 and a pump 512. Elements 504-512 are fluidly coupled in series: filter and valve assembly 504 is fluidly coupled to pre-concentrator 506 by fluid connection 516, pre-concentrator 506 is fluidly coupled to gas chromatograph 508 by fluid connection 518, gas chromatograph 508 is fluidly coupled to detector array 510 by fluid connection 520, and detector array 510 is coupled to pump 512 by fluid connection 522. In one embodiment of device 500 elements 504-512 can be micro-electro-mechanical (MEMS) elements or MEMS-based elements, meaning that some parts of each device can be MEMS and other parts not. In other embodiments of device 500, some or all of elements 504-512 need not be MEMS or MEMS-based, but can instead be some non-MEMS chip scale device.

As indicated by the arrows in the figures, the fluid connections between elements 504-512 allow a fluid (e.g., one or more gases) to enter filter and valve assembly 504 through inlet 514, flow though elements 504-512, and finally exit pump 512 through outlet 524. Fluid handling assembly 501 also includes a shroud or cover 513 that protects individual elements 504-512. In the illustrated embodiment, channels formed in shroud 513 provide the fluid connections between the elements, but in other embodiments the fluid connections between elements can be provided by other means, such as tubing. In still other embodiments shroud 513 can be omitted.

Controller 526 is communicatively coupled to the individual elements within fluid handling assembly 501 via traces 530 such that it can send control signals and/or receive feedback signals from the individual elements. In one embodiment, controller 526 can be an application-specific integrated circuit (ASIC) designed specifically for the task, for example a CMOS controller including processing, volatile and/or non-volatile storage, memory and communication circuits, as well as associated logic to control the various circuits and communicate externally to the elements of fluid handling assembly 501. In other embodiments, however, controller 526 can instead be a general-purpose microprocessor in which the control functions are implemented in software. In the illustrated embodiment controller 526 is electrically coupled to the individual elements within fluid handling assembly 501 by conductive traces 530 on the surface or in the interior of substrate 502, but in other embodiments controller 526 can be coupled to the elements by other means, such as optical.

Readout and analysis circuit 528 is coupled via traces 532 to an output of detector array 510 such that it can receive data signals from individual sensors within detector array 510 and process and analyze these data signals. In one embodiment, readout and analysis circuit 528 can be an application-specific integrated circuit (ASIC) designed specifically for the task, such as a CMOS controller including processing, volatile and/or non-volatile storage, memory and communication circuits, as well as associated logic to control the various circuits and communicate externally. In other embodiments, however, readout and analysis circuit 528 can instead be a general-purpose microprocessor in which the control functions are implemented in software. In some embodiments readout and analysis circuit 528 can also include signal conditioning and processing elements such as amplifiers, filters, analog-to-digital converters, etc., for both pre-processing of data signals received from detector array 510 and postprocessing of data generated or extracted from the received data by readout and analysis circuit 528.

In operation of device 500, the system is first powered up and any necessary logic (i.e., software instructions) is loaded into controller 526 and readout and analysis circuit 528 and initialized. After initialization, the valve in filter and valve unit 504 is opened and pump 512 is set to allow flow through the fluid handling assembly. Fluid is then input to fluid handling assembly 501 through inlet 514 at a certain flow rate and/or for a certain amount of time; the amount of time needed will usually be determined by the time needed for pre-concentrator 506 to generate adequate concentrations of the particular chemicals whose presence and/or concentration are being determined. As fluid is input to the system through inlet 514, it is filtered by filter and valve assembly 504 and flows through elements 504-512 within fluid handling assembly 501 by virtue of the fluid connections between these elements. After flowing through elements 504-512, the fluid exits the fluid handling assembly through exhaust 524.

After the needed amount of fluid has been input through inlet 514, the valve in filter and valve assembly 504 is closed to prevent further input of fluid. After the valve is closed, a heater in pre-concentrator 506 activates to heat the pre-concentrator. The heat releases the chemicals absorbed and concentrated by the pre-concentrator. As the chemicals are released from pre-concentrator 506, pump 512 is activated to draw the released chemicals through gas chromatograph 508 and detector array 510 and output the chemicals through exhaust 524. Activation of pump 512 also prevents backflow through fluid handling assembly 501.

As the chemicals released from pre-concentrator 506 are drawn by pump 512 through gas chromatograph 508, the chromatograph separates different chemicals from each other in the time domain-that is, different chemicals are output from the gas chromatograph at different times. As the different chemicals exit gas chromatograph 508 separated in time, each chemical enters detection array 510, where sensors in the detection array detect the presence and/or concentration of each chemical. The time-domain separation performed in gas chromatograph 508 substantially enhances the accuracy and sensitivity of detection array 510, since it prevents numerous chemicals from entering the detection array at the same time and thus prevents cross-contamination and potential interference in the sensors within the array.

As individual sensors within detection array 510 interact with the entering time-domain-separated chemicals, the detection array senses the interaction and outputs a signal to readout and analysis circuit 528, which can then use the signal to determine presence and/or concentration of the chemicals. When readout and analysis circuit 528 has determined the presence and/or concentration of all the chemicals of interest it can use various analysis techniques, such as correlation and pattern matching, to extract some meaning from the particular combination of chemicals present and their concentrations.

Figure 6A:
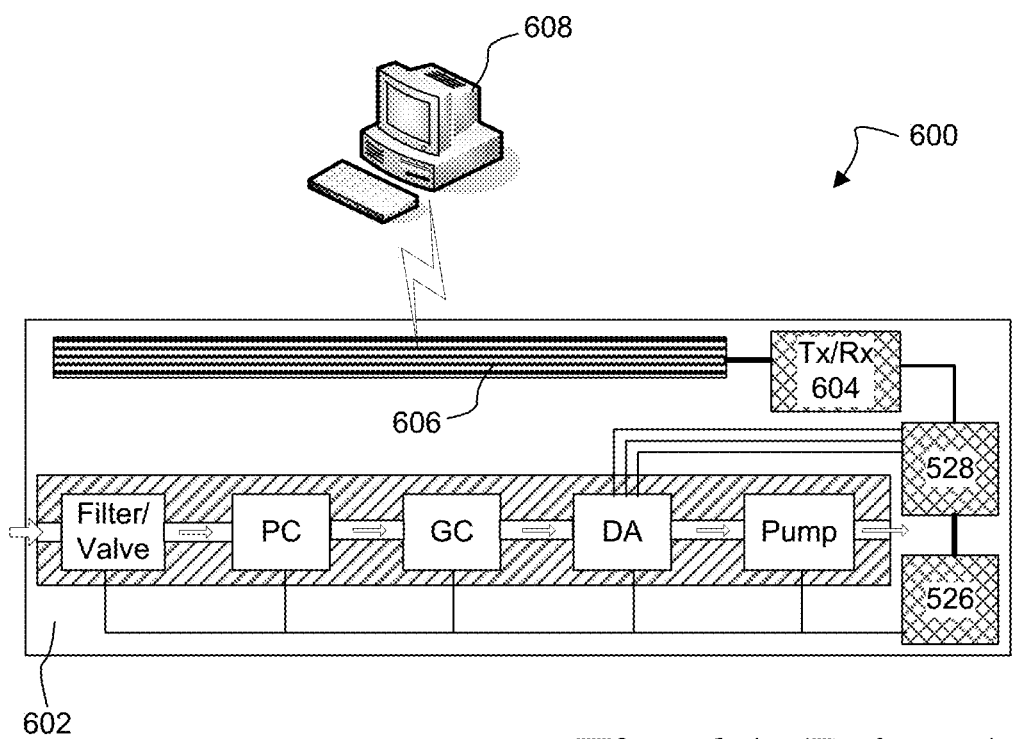
FIGS. 6A-6B are plan-view schematics of other embodiments of a multiple-gas analysis system that can be used in the indoor and outdoor gas monitoring and control systems of FIGS. 2-3.

FIG. 6A illustrates an embodiment of a multiple-gas analysis system or detector 600. MGD 600 is in most respects similar to device 500. The primary difference between device 600 and device 500 is the presence in device 600 of a wireless transceiver circuit 604 and an antenna 606 mounted on substrate 602. Wireless transceiver circuit 604 can both transmit (Tx) data and receive (Rx) data and is coupled to reading and analysis circuit 528 and antenna 606. In one embodiment of MGD 600, transceiver 604 can be used to wirelessly transmit data from reading and analysis circuit 528 to a computer 608, which can be located in the data and control center of systems 200 or 300 and can perform the previously-described functions of the data center.

Figure 6B:
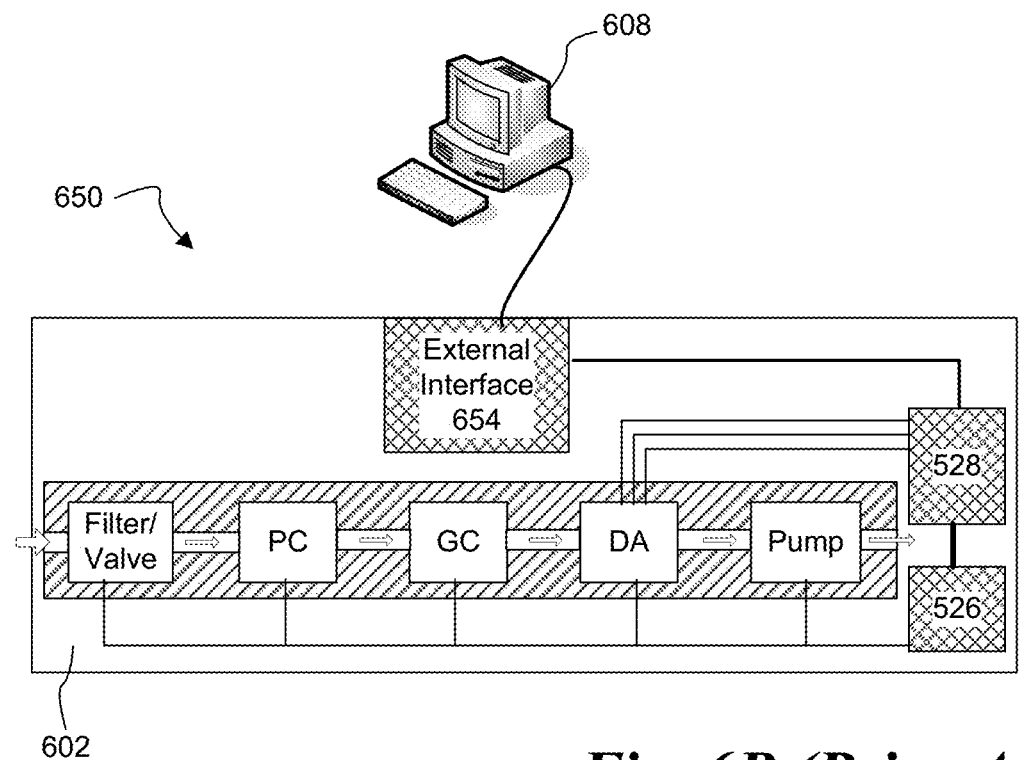

FIG. 6B illustrates an alternative embodiment of a multiple-gas analysis device 650. MGD 650 is in most respects similar to MGD 600. The primary difference between MGDs 650 and 600 is that the wireless transceiver circuit 604 and antenna 606 are replaced with a hardware data interface 654 coupled to reading and analysis circuit 528. In one embodiment, hardware data interface 654 could be a network interface card, but in other embodiments hardware data interface can be an Ethernet card, a simple cable plug, etc. External devices can be connected to device 650 through traditional means, such as cables. Although it has a different communication interface, MGDs 650 and 600 have all the same functionality. As with system 500, in system 600 MEMS-based gas analysis device 650 can transmit data to, and receive data from, one or both of a computer 608, which can be located in the data and control center of systems 200 or 300 and can perform the previously-described functions of the data center.

Figure 7:
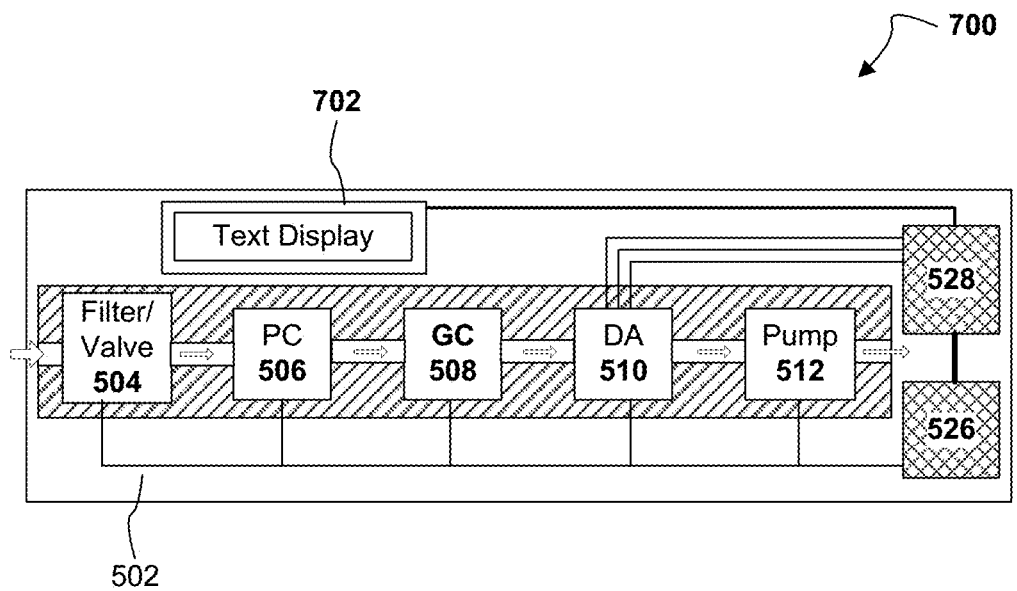
FIGS. 7-8 are schematic views of other embodiment of a multiple-gas analysis system that can be used in the indoor and outdoor gas monitoring and control systems of FIGS. 2-3.

FIG. 7 illustrates an alternative embodiment of a multiple-gas analysis device 700. MGD 700 is in most respects similar to device 500. The primary difference between MGD 700 and device 500 is that MGD 700 includes an on-board display 702 for conveying to a user the results of the analysis performed by reading and analysis circuit 528. The illustrated embodiment uses an on-board text display 702, for example an LED or LCD screen that can convey text information to a user. In another embodiment a simpler display can be used, such as one with three lights that indicate a positive, negative, or indeterminate result depending on which light is switched on. For example, if in response to detection of contaminants it is necessary to send an inspection team to investigate, the device can provide information to the inspectors.

Figure 8:
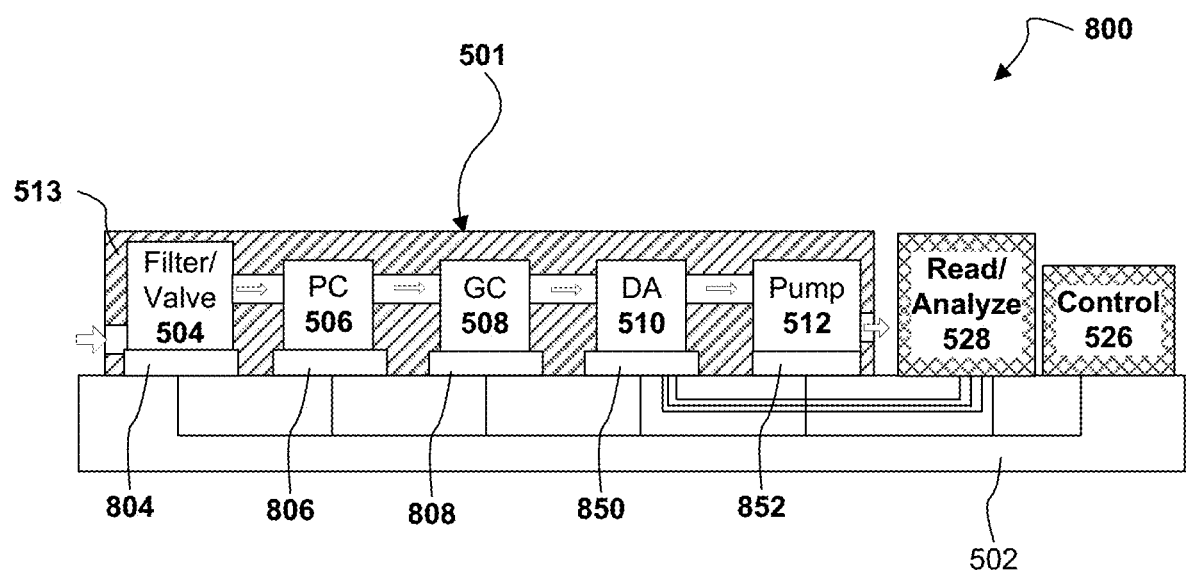

FIG. 8 illustrates an alternative embodiment of a multi-gas analysis device 800. MGD 800 is in most respects similar to MGD 500. The primary difference between device 800 and device 500 is that in device 800 one or more elements of fluid handling assembly 501 are replaceable. In the illustrated embodiment, the elements are made replaceable by mounting them onto substrate 502 using sockets: filter and valve assembly 504 is mounted to substrate 502 by socket 804, pre-concentrator 506 is mounted to substrate 502 by socket 806, gas chromatograph 508 is mounted to substrate 502 by socket 808, detector array 510 is mounted to substrate 502 by socket 850, and pump 512 is mounted to substrate 502 by socket 852. In one embodiment, sockets 804-812 are sockets, such as zero insertion force (ZIF) sockets that permit easy replacement by a user, but in other embodiments other types of sockets can be used. Although the illustrated embodiment shows all the components of fluid handling assembly 501 being replaceable, in other embodiments only some of the components, such as pump 512 and detector array 510, can be made replaceable. The benefit of having replaceable fluid handling elements is that the MGD can be easily repaired if broken or can be easily converted to detect different gases or combinations of gases without the need to replace the entire MGD.

The above description of illustrated embodiments of the invention, including what is described in the abstract, is not intended to be exhaustive or to limit the invention to the precise forms disclosed. While specific embodiments of, and examples for, the invention are described for illustrative purposes, various equivalent modifications are possible within the scope of the claims, as those skilled in the relevant art will recognize. These modifications can be made in light of the above detailed description.

The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

The invention claimed is:

1. An apparatus comprising:
   a plurality of multiple-gas analysis devices positioned at different locations within a room, each multiple-gas analysis device capable of detecting a presence, concentration, or both, of one or more designated gases, wherein:
      at least one of the plurality of multiple-gas analysis devices is fluidly coupled to multiple sampling tubes that extend from the multiple-gas analysis device to a sampling end, the sampling ends of at least two of the multiple sampling tubes being within the same room as the multiple-gas analysis device from which they extend, and
      at least two of the multiple sampling tubes include a sorbent trap, wherein the at least two sorbent traps collect samples simultaneously and release the collected samples sequentially for analysis by the multiple-gas analysis device;
   a data and control center communicatively coupled to each of the plurality of multiple-gas analysis devices, the data and control center including logic that, when executed, allows the data and control center to:
      perform automatic data analysis on the reliability of the output from each multiple-gas analysis device to ensure no false data due to the multiple-gas analysis device or data communication glitches;
      monitor readings from the plurality of multiple-gas analysis devices, and
      if any readings indicate the presence of one or more contaminants in the room, identifying the source of the contaminants based on the readings from the plurality of multiple-gas analysis devices.

2. The apparatus of claim 1, further comprising at least one anemometer positioned in the room and communicatively coupled to the data and control center.

3. The apparatus of claim 2 wherein each anemometer is paired with a corresponding multiple-gas analysis device.

4. The apparatus of claim 2 wherein each anemometer is paired with a plurality of multiple-gas analysis devices.

5. The apparatus of claim 2 wherein a plurality of anemometers are paired with each multiple-gas analysis device.

6. The apparatus of claim 2 wherein the at least one anemometer can measure at least air speed and direction.

7. The apparatus of claim 6 wherein the at least one anemometer can further measure air temperature, air pressure, and humidity.

8. The apparatus of claim 1 wherein the data and control center includes data on topology within the room.

9. The apparatus of claim 1 wherein the data and control center is communicatively coupled to a ventilation system of the room and can control operation of the ventilation system.

10. The apparatus of claim 1 wherein the at least one multiple-gas analysis device is fluidly coupled to a filter so that the at least one multiple-gas analysis device can sample air flowing through the filter.

11. The apparatus of claim 1 wherein all of the multiple sampling tubes include a sorbent trap.

12. The apparatus of claim 1 wherein each of the plurality of multiple-gas analysis devices is paired with a process facility within the room.

13. The apparatus of claim 12 wherein the data and control center is communicatively coupled to each process facility and can control the operation of the process facility.

14. The apparatus of claim 12 wherein at least one multiple-gas analysis device is fluidly coupled to one or more sampling tubes that extend from the multiple-gas analysis device to a location in or near the associated process facility.

15. The apparatus of claim 1 wherein at least one of the plurality of multiple-gas analysis devices comprises:
   a substrate;
   a gas chromatograph having a fluid inlet and a fluid outlet and being mounted to the substrate;
   a detector array having a fluid inlet and a fluid outlet and being mounted to the substrate, wherein the fluid inlet of the detector array is fluidly coupled to the fluid outlet of the gas chromatograph;
   a control circuit coupled to the gas chromatograph and to the detector array, wherein the control circuit can communicate with the gas chromatograph and to the detector array; and
   a readout circuit coupled to the detector array and to the control circuit, wherein the readout circuit can communicate with the control circuit and the detector array.

* * * * *